US006426505B1

United States Patent
Rao et al.

(10) Patent No.: US 6,426,505 B1
(45) Date of Patent: Jul. 30, 2002

(54) PHASE-MODULATION FLUOROMETER AND METHOD FOR MEASURING NANOSECOND LIFETIMES USING A LOCK-IN AMPLIFIER

(75) Inventors: Govind Rao, Columbia; Peter Harms, Baltimore, both of MD (US)

(73) Assignees: University of Maryland Biotechnology Institute, College Park; University of Maryland Baltimore County, Baltimore, both of MD (US)

(*) Notice: Subject to any disclaimer, the term of this patent is extended or adjusted under 35 U.S.C. 154(b) by 0 days.

(21) Appl. No.: 09/487,275

(22) Filed: Jan. 19, 2000

(51) Int. Cl.[7] ............................................... G01N 21/64
(52) U.S. Cl. ............................. 250/458.1; 250/459.1; 356/318
(58) Field of Search ........................ 250/458.1, 459.1, 250/461.1, 461.2, 361 R; 356/318, 417; 435/288.7; 422/82.08

(56) References Cited

U.S. PATENT DOCUMENTS

| | | | |
|---|---|---|---|
| 3,354,315 A | 11/1967 | Preston et al. | 250/217 |
| 4,059,405 A | 11/1977 | Sodickson et al. | 23/230 |
| 5,141,312 A | 8/1992 | Thompson et al. | 356/218 |
| 5,293,210 A | 3/1994 | Berndt | 356/39 |
| 5,308,771 A | 5/1994 | Zhou et al. | 436/39 |
| 5,315,993 A | 5/1994 | Alcala | 128/634 |
| 5,504,337 A | 4/1996 | Lakowicz et al. | 250/461.2 |
| 5,580,784 A | 12/1996 | Berndt | 435/288.7 |
| 5,593,854 A | 1/1997 | Berndt | 435/31 |
| 5,686,300 A | 11/1997 | Berndt | 435/287.5 |
| 5,818,582 A | 10/1998 | Fernandez et al. | 356/318 |
| 5,824,270 A | 10/1998 | Rao | 422/82.09 |
| 5,863,460 A | 1/1999 | Slovacek et al. | 252/301.35 |
| 5,876,672 A | 3/1999 | Dandliker et al. | 422/82.08 |
| 5,911,952 A | 6/1999 | Tsuji | 422/82.08 |

OTHER PUBLICATIONS

Harms, Peter; Sipior, Jeffrey; Ram, Natraj; Carter, Gary; Rao, Govind: Low Cost phase–modulation measurements of nanosecond fluorescence lifetimes using a lock–in amplifier, Rev. Sci. Instrum., vol. 70, No. 2, Feb. 1999, pp. 1535–1539.
Lakowicz, Joseph; Soper, Steven, Thompson, Richard, editors: Advances in Fluorescence Sensing Technology IV, SPIE Proceedings of SPIE vol. 3602, Jan. 24–27, 1999, pp. 52–59.

(List continued on next page.)

*Primary Examiner*—Georgia Epps
*Assistant Examiner*—Richard Hanig
(74) *Attorney, Agent, or Firm*—Sughrue Mion, PLLC

(57) ABSTRACT

A low cost apparatus and method for measuring nanosecond luminescence lifetimes with a modulated LED light source that is driven by a lock-in amplifier. The lock-in amplifier provides both a DC bias and an AC signal used to modulate the intensity of an LED source light at a wavelength capable of exciting a photoluminescent species. Excitation of the photoluminescent species produces a corresponding emission. The emission, which can be detected in a variety of ways, was measured by a photomultiplier tube with the resulting signal being sent through a DC block back to the lock-in amplifier with no external signal processing or heterodyning required. The measuring process can be controlled by a computer through a GPIB, USB, serial or similar connection. The computer can also be used to correct for the most common sources of error, namely coherent pickup and stray ambient light. The apparatus without the computer has a component cost of less than US $10,000. Several standard fluorophores were measured with results comparable to research-grade cross-correlation phase fluorometers for frequencies up to 100 MHz. The apparatus is portable, consumes little power, and can be easily configured for use with fiber optics, making it ideal for use with fluorescence lifetime based sensors.

20 Claims, 11 Drawing Sheets

OTHER PUBLICATIONS

Bambot, S., R. Holavanahali, J.R. Lakowicz, G.M. Carter and G. Rao, Phase Fluorometric Sterilizable Optical Oxygen Sensor, Biotechnology and Bioengineering 43, 1139–1145, 1994.

Chang, Q., L. Randers–Eichhorn, J.R. Lakowicz, G. Rao, Steam–Sterilizable Fluorescence Lifetime–Based Sensing Film for Dissolved Carbon Dioxide, Biotechnol. Prog. 14, 326–331, 1998.

Gratton, E. and M. Limkeman, A Continuously Variable Frequency Cross–Correlation Phase Fluorometer with Picosecond Resolution, Biophys. J., 315–324, 1983.

Gruber, W.R., P. O'Leary, O.S. Wolfbeis, Detection of Fluorescence Lifetime Based on Solid–State Technology, and Its Application to Optical Sensing, Proc. SPIE 2388, 148–158, 1995.

Gryczynski, I., J. Kusba, J.R. Lakowicz, Effect of Light Quenching on the Emission Spectra and Intensity Decays of Fluorophore Mixtures, J.Fluorescence 7, 167–183, 1997.

Holavanahali, R., M. Romauld, G.M. Carter, G. Rao, J. Sipior, J.R. Lakowicz and J.D. Bierlein, Directly Modulated Diode Laser Frequencey–Doubled in a KTP Waveguide as an Excitation Source for $CO_2$ and $O_2$ Phase Fluorometric Sensors, J. Biomed. Optics 1, 124–130, 1996.

Holst, G.A., T. Koster, E. Voges, D. Lubbers, FLOX an Oxygen–Flux–Measuring System Using a Phase–Modulation Method to Evaluate the Oxygen–Dependent Fluorescence Lifetime, Sens. Actuators B 29, 231–9, 1995.

Lakowicz, J.R. and I. Gryczynski, Frequency–Domain Fluorescence Spectroscopy, in Topics in Fluorescence Spectroscopy, vol. 1 Techniques, (J.R. Lakowicz, Ed.), 293–335, 1991.

Lakowicz, J.R., G. Laczko, I. Gryczynski, 2–GHz Frequency–Domain Fluorometer, Rev. Sci. Instrum. 57, 2499–2506, 1986.

Lakowicz, J.R. and B. Maliwal, Construction and Performance of a Variable–Frequency Phase–Modulation Fluorometer, Biophysical Chemistry 21, 61–78, 1985.

Lakowicz, J.R. and B. Maliwal, Optical Sensing of Glucose Using Phase–Modulation Fluorimetry, Anal. Chim. Acta. 271, 155–164, 1993.

Levy, R., E.F. Guignon, S. Cobane, E. St. Louis and S.M. Femandez, Compact, Rugged and Inexpensive Frequency-Domain Fluorometer, SPIE 2980, 81–89, 1997.

Murtagh, M. T., D.E. Acklev, M.R. Shahriari, Development of a Highly Sensitive Fiber Optic $O_2$/DO Sensor Based on a Phase Modulation Technique, Electronics Letters 32, 477–479, 1996.

Ozinskas, A, H. Malak, J. Joshi, H. Szmacinski, J. Britz, R. Thompson, P. Koen and J.R. Lakowicz, Homogeneous Model Immunoassay of Thyroxine by Phase–Modulation Fluorescence Spectroscopy, Anal. Biochem. 213, 264–270, 1993.

Spencer, R.D. and G. Weber, Measurement of Sub–Nanosecond Fluorescence Lifetime with a Cross–Correlation Phase Fluorometer, Ann. N. Y. Acad. Sci. 158, 361–376, 1969.

Sipior, J., G. Carter, J.R. Lakowicz, G. Rao, Single Quantum Well Light Emitting Diodes Demonstrated as Excitation Sources for Nanosecond Phase–Modulation Fluorescence Lifetime Measurements, Rev. Sci. Instrum. 67, 3795–3798, 1996.

Szmacisnki, H., J.R. Lakowicz, Optical Measurements of pH Using Fluorescence Lifetimes and Phase–Modulation Fluorometry, Anal. Chem. 65, 1668–1674, 1993.

Thompson, R.B., Z. Ge, M. W. Patchan and C.A. Fierke, Performance Enhancement of Fluorescence Energy Transfer–Based Biosensors by Site–Directed Mutagenesis of the Transducer, J. Biomed. Optics 1, 131–137, 1996.

Zhang, Z., K.T.V. Grattan, A.W. Palmer, A Novel Signal Processing Scheme for a Fluorescence Based Fiber–Optic Temperaure Sensor, Rev. Sci. Instrum. 62, 1735–42, 1991.

PHASE-MODULATION FLUOROMETER AND METHOD FOR MEASURING NANOSECOND LIFETIMES USING A LOCK-IN AMPLIFIER

FEDERAL SPONSORSHIP OF INVENTION

The U.S. Government has a paid-up license in this invention as provided by the terms of agreements numbers BES-9413262 and RR-10955 awarded under the Merit Review Program by the National Science Foundation and the National Institute of Health, respectively.

BACKGROUND OF THE INVENTION

1. Field of the Invention

This invention is directed to an apparatus and method for the measurement of photoluminescent lifetimes. More specifically, the invention concerns a low cost portable frequency-domain phase fluorometer which operates at a frequency of up to 200 MHz without the need for a cross-correlation detection.

2. Prior Art

The contents of all cited references including literature references, issued patents, published patent applications as cited throughout this application are readily available to those skilled in the art and are hereby expressly incorporated herein by reference as though they were set forth herein in their entirety.

LITERATURE REFERENCES

Anghel, F., C. Iliescu, K. T. V. Grattan, A. W. Palmer and Z. Y. Zhang, "Fluorescent-Based Lifetime Measurement Thermometer for Use at Subroom Temperatures (200–300 K)", Rev. Sci. Instrum. 66, 2611–2614, 1995.

Bambot, S., R. Holavanahali, J. R. Lakowicz, G. M. Carter and G. Rao, "Phase Fluorometric Sterilizable Optical Oxygen Sensor", Biotechnology and Bioengineering 43, 1139–1145, 1994.

Chang, Q., L. Randers-Eichhorn, J. R. Lakowicz, G. Rao, "Steam-Sterilizable Fluorescence Lifetime-Based Sensing Film for Dissolved Carbon Dioxide", Biotechnol. Prog. 14, 326–331, 1998.

Gratton, E. and M. Limkeman, "A Continuously Variable Frequency Cross-Correlation Phase Fluorometer with Picosecond Resolution," Biophys. J., 315–324, 1983.

Gruber, W. R., P. O'Leary, O. S. Wolfbeis, "Detection of Fluorescence Lifetime Based on Solid-State Technology, and Its Application to Optical Sensing", Proc. SPIE 2388, 148–158, 1995.

Gryczynski, I., J. Kusba, J. R. Lakowicz, "Effect of Light Quenching on the Emission Spectra and Intensity Decays of Fluorophore Mixtures", J. Fluorescence 7, 167–183, 1997.

Holavanahali, R., M. Romauld, G. M. Carter, G. Rao, J. Sipior, J. R. Lakowicz and J. D. Bierlein, "Directly Modulated Diode Laser Frequency-Doubled in a KTP Waveguide as an Excitation Source for $CO_2$ and $O_2$ Phase Fluorometric Sensors", J. Biomed. Optics 1, 124–130, 1996.

Hoist, G. A., T. Koster, E. Voges, D. Lubbers, "FLOX an Oxygen-Flux-Measuring System Using a Phase-Modulation Method to Evaluate the Oxygen-Dependent Fluorescence Lifetime", Sens. Actuators B 29, 231–9, 1995.

Lakowicz, J. R., *Principles of Fluorescence Spectroscopy*. Plenum Press, New York, 1983.

Lakowicz, J. R. and I. Gryczynski, "Frequency-Domain Fluorescence Spectroscopy", in *Topics in Fluorescence Spectroscopy*, Vol. 1 Techniques, (J. R. Lakowicz, Ed.), 293–335, 1991.

Lakowicz, J. R., G. Laczko, I. Gryczynski, "2-GHz Frequency-Domain Fluorometer", Rev. Sci. Instrum. 57, 2499–2506, 1986.

Lakowicz, J. R. and B. Maliwal, "Construction and Performance of a Variable-Frequency Phase-Modulation Fluorometer", Biophysical Chemistry 21, 61–78, 1985.

Lakowicz, J. R. and B. Maliwal, "Optical Sensing of Glucose Using Phase-Modulation Fluorimetry", Anal. Chim. Acta. 271, 155–164, 1993.

Levy, R., E. F. Guignon, S. Cobane, E. St. Louis and S. M. Femandez, "Compact, Rugged and Inexpensive Frequency-Domain Fluorometer", SPIE 2980, 81–89, 1997.

Murtagh, M. T ., D. E. Acklev, M. R. Shahriari, "Development of a Highly Sensitive Fiber Optic $O_2$/DO Sensor Based on a Phase Modulation Technique", Electronics Letters 32, 477–479, 1996.

Ozinskas, A, H. Malak, J. Joshi, H. Szmacinski, J. Britz, R. Thompson, P. Koen and J. R. Lakowicz, "Homogeneous Model Immunoassay of Thyroxine by Phase-Modulation Fluorescence Spectroscopy", Anal. Biochem. 213, 264–270, 1993.

Spencer, R. D. and G. Weber, "Measurement of Sub-Nanosecond Fluorescence Lifetime with a Cross-Correlation Phase Fluorometer", Ann. N. Y. Acad. Sci. 158, 361–376, 1969.

Sipior, J., G. Carter, J. R. Lakowicz, G. Rao, "Single Quantum Well Light Emitting Diodes Demonstrated as Excitation Sources for Nanosecond Phase-Modulation Fluorescence Lifetime Measurements", Rev. Sci. Instrum. 67, 3795–3798, 1996.

Szmacisnki, H., J. R. Lakowicz, "Optical Measurements of pH Using Fluorescence Lifetimes and Phase-Modulation Fluorometry", Anal. Chem. 65, 1668–1674, 1993.

Thompson, R. B., Z. Ge, M. W. Patchan and C. A. Fierke, "Performance Enhancement of Fluorescence Energy Transfer-Based Biosensors by Site-Directed Mutagenesis of the Transducer", J. Biomed. Optics 1, 131–137,1996.

Zhang, Z., K. T. V. Grattan, A. W. Palmer, "A Novel Signal Processing Scheme for a Fluorescence Based Fiber-Optic Temperature Sensor", Rev. Sci. Instrum. 62, 1735–42, 1991.

U.S. Patents

| | | |
|---|---|---|
| 5,141,312 | August 25, 1992 | Thompson et al. |
| 5,504,337 | April 2, 1996 | Lakowicz et al. |
| 5,818,582 | October 6, 1998 | Femandez et al. |

Numerous chemical and biochemical research tools, remote sensing devices, and immunodiagnostic test methods are based on some form of photoluminometric analysis (e.g., fluorometry and phosphorimetry). Although the disclosure herein primarily focuses on a fluorometric apparatus and method of analysis, the terms used herein such as fluroescence, fluorophore and fluorometer, are to be construed to include the meaning of phosphorescence, phosphor and phosphorimeter, respectively.

Fluorometry offers a wide range of advantages over other spectroscopic methods (e.g., colorimetry). These advantages include low detection limits and the potential for minimally invasive measurements in biological samples. However, simple intensity based methods are prone to artifacts because any change in fluorescence intensity, regardless of origin, can flaw the analysis. Specifically, intensity measurements can suffer from interferences caused by light scattering, variations in the intensity of the source or excitation light, photobleaching, contaminating chromophores, or changes in the collection geometries. To circumvent the limitations of intensity measurements, Lakowicz and other researchers developed methods based on measuring the fluorescence lifetime of a fluorophore in the time or frequency domain (Lakowicz et al. (1986); Zhang et al. (1991); Gruber et al. (1995); Holst et al. (1995); and Murtagh et al. (1996)). Fluorescence lifetime analysis has been used, for example, to study: rotational and molecular diffusion; energy transfer kinetics and other excited state reactions; and collisional quenching (Lakowicz, 1983). Fluorescence lifetime analysis has also been used in the development of immunoassays (Ozinskas, 1993); sensors for the measurement of pH (Szmacisnki et al., 1993); temperature (Anghel et al., 1995); glucose (Lakowicz and Maliwal, 1993); metal ions (Thompson et al., 1996); oxygen (Bambot et al., 1994); and carbon dioxide (Holavanahali et al., 1993).

Various methods for measuring fluorescence lifetimes are common to the art and include both time domain and frequency domain methods. In time domain methods, the fluorescence lifetime of a sample is determined from an analysis of the fluorescence decay that is elicited by a pulsed excitation. In general, a sample is excited with a brief pulse of light and the time-dependent decay in fluorescence intensity is measured. However, the measurement of the decay in fluorescence intensity is difficult as light sources typically yield pulses with durations of several nanoseconds. As a result, one must either correct for the pulse width or select an alternative light source which can yield pulses of a duration shorter than the average lifetime being measured. Generally such pulsed picosecond light sources are not only expensive but add to the technical complexity of the system. A further difficulty of time domain methods is the need to measure the entire duration of the time-resolved fluorescence decay. This difficulty is generally minimized by exciting the sample with repetitive pulses that are spaced at time intervals greater than a factor of five times the decay time, to avoid overlap of the decay pulses. However, if repetitive pulses are used, the decay in fluorescence intensity must be reconstructed using either a stroboscopic or photon counting method (Lakowicz, 1983). Further, one must also correct for the finite width of the light pulse and the response time of the detection system when using a photon counting technique (e.g., Time-Correlated Single Photon Counting Technique (TCSPC)) in order to obtain the true fluorescence decay pulse.

Frequency domain or phase-modulation methods do not require corrections for the finite width of the excitation pulses or the time response of the detection system. Further, frequency domain or phase-modulation methods have the advantage of lower cost electronics than that required for decay time measurement as the excitation light pulse can be longer in duration. Typically, in frequency domain or phase modulation methods, the intensity of the excitation light is pulsed or modulated sinusoidally, resulting in fluorescence at the same circular frequency as the excitation light. However, due to the finite duration of the fluorophore's excited state, the emitted fluorescence lags in phase by an angle, $\phi$, as compared to the circular frequency of the excitation light. In addition, the depth of modulation compared to the excitation is also reduced. A demodulation factor, m, is defined by the equation:

$$m=(B/A)/(b/a) \tag{1}$$

where "a" is the average value of the emitted fluorescence; "a" is the average value of the excitation light; "B" is the amplitude of the peak emission above its average value; and "b" is the amplitude of the peak excitation above its average value.

The circular frequency of the excitation light $\omega$ can be expressed by the equation:

$$\omega=(2\pi) \text{ (frequency)} \tag{2}$$

where the frequency is expressed in Hz. Typically, both the phase angle $\phi$ and the demodulation factor m which corresponds to the reduction in the depth of modulation compared to the excitation are measured and used to calculate the phase $\tau_p$ and modulation $\tau_m$ lifetimes of the sample, respectively. This provides two independent measurements of the fluorescence lifetime, giving an added degree of robustness to the measurement. The phase $\tau_p$ lifetime can be calculated using the equation:

$$\tau_p=(\omega^{-1})(\tan\phi) \tag{3}$$

whereas, the modulation $\tau_m$ lifetime can be calculated using the equation:

$$\tau_m=(\omega^{-1})[(1/m^2)-1]^{1/2} \tag{4}$$

Multifrequency measurements in combination with non-linear least squares curve fitting techniques are used in multi-exponential decay analyses of heterogeneous samples. Plots of phase angle vs. modulation frequency, or demodulation vs. modulation frequency are used in fluorescence lifetime analysis. This multi-exponential decay analysis is based on known theoretical considerations by and between phase angle and modulation with fluorescence lifetime (Lakowicz and Gryczynski, 1991).

Frequency domain or phase-modulation methods have also been successfully used in remote sensing applications. A variety of sensors have been developed which are responsive to changes in environmental factors such as temperature and pH. Although the time dependent emission of fluorescence by a fluorophore can usually be characterized by a single exponential decay constant, multiple decay constants can result from either changes in a fluorophore's environment, or as the result of various excited state processes. As with heterogeneous fluorescent samples, multi-frequency measurements in combination with non-linear least squares curve fitting techniques can be used in the analysis. Alternatively, an average lifetime measurement can provide a suitable metric that correlates with the environmental factor of interest (Levy et al., 1997). Further, fluorescence lifetime based sensors avoid the problems associated with photobleaching and excitation source intensity which are common to intensity based sensor designs (Lakowicz, 1984).

To date the major drawback of fluorescence lifetime analysis is the component cost of the system. Even the lower component cost of phase-modulation as compared to pulse systems is beyond the budget of most labs, especially for the measurement of nanosecond lifetimes. Less expensive and simpler instrument designs can be used with long lifetime fluorophores but these fluorophores do not have the sensing capability that conventional nanosecond probes offer. Fluorophores with lifetimes on the order of hundreds of nanoseconds to a few microseconds have been measured with low-cost lock-in amplifier based systems, albeit only for phase angle measurements (Bambot et al. (1994)).

The components and costs associated with the construction of a variable frequency phase-modulation fluorometer are well known. For example see Lakowicz and Maliwal (1985). The instrument described provides modulation frequencies from 1 to 200 MHz and measures phase angles and demodulation factors using a cross-correlation detection method. The cross-correlation technique is well known to those skilled in the art and is described in Spencer and Weber, "Measurement of Sub-Nanosecond Fluorescence Lifetime with a Cross-Correlation Phase Fluorometer" (1969). The basic cross-correlation phase fluorometer includes a light source (helium-cadmium laser), an electro-optic modulator, two frequency synthesizers, two radio frequency power amplifiers, and various optical and electronic parts for a component cost in excess of US $50,000. Current commercially available multifrequency fluorometers are priced on the order of US $100,000.

A diode-laser based cross-correlation phase fluorometer suitable for single frequency sensor applications has recently been described in the article by Levy et al. (1997). This system is an inexpensive alternative to the multifrequency fluorometers described above. In contrast to conventional cross-correlation methods in which the signal frequency is generated as a difference in the frequency of two high frequency sources, the instrument described in Levy et al. (1997) uses a single sideband technique in which the signal frequency is generated as the sum of two different frequencies. However, this approach is limited with respect to multifrequency applications. Specifically, given their method of down-conversion, corrections for optically or electronically induced phase shifts common to all phase fluorometers have to be made at each tested frequency. Furthermore, the instrument described in Levy et al. (1997) provides a lifetime measurement based on just phase angle.

The high cost and complexity of performing lifetime measurements at multiple frequencies presented an opportunity for the development of an inexpensive and practical instrument for the measurement of fluorescence lifetimes using a phase-modulation method. Recent advances in digital signal processors has produced a new class of lock-in amplifiers and provided the core component to the present invention. The SR844 RF lock-in amplifier (Stanford Research Systems, Sunnyvale, Calif.) is commercially available and representative of this new class. While most lock-in amplifiers have a maximum frequency of 100 kHz, the SR844 can measure up to 200 MHz.

SUMMARY OF THE INVENTION

The present invention relates to an apparatus and method for measuring nanosecond photoluminescence lifetimes. The basic apparatus presents a low cost alternative for the measurement of photoluminescence lifetimes using a multiple frequency phase sensitive detection technique. Unlike the prior art, the use of multiple mixers in a lock-in amplifier to get baseband signals in quadrature obviates the need to re-calibrate at each frequency, providing a much simpler method for multifrequency applications. Further, lifetime analysis with the present invention are based on two independent measurements, phase angle and modulation. It is the development of high frequency lock-in amplifiers coupled with the emergence of a wide range of low cost light sources (e.g., LEDs) which can be modulated at high frequencies, that have enabled the design and construction of a variable frequency phase-modulation fluorometer in accordance with the present invention at a component cost of under US $10,000.

As used herein, photoluminescence means any of a group of processes whereby a material is excited by radiation such as light, raised to an excited electronic or vibronic state, and subsequently re-emits that excitation energy as a photon of light. These processes include fluorescence and phosphorescence. Fluorescent emissions accompany the descent of excited state electrons from paired "singlet" states to lower states of the same multiplicity; an "allowed" quantum-mechanics transition. In contrast, phosphorescent emissions accompany the descent of excited state electrons from unpaired "triplet" states to lower states of a different multiplicity; a "forbidden" quantum-mechanics transition.

Since in any given sample more than one lifetime can be present, the term "lifetime" means and includes the term "lifetimes" and the term "lifetimes" means and includes the term "lifetime", so as to include all possibilities under the circumstances, including multiple lifetimes that are present in the particular sample under consideration.

The present invention provides a low cost alternative to the complex multifrequency phase-modulation instruments that are commercially available. The level of complexity and component cost of an instrument according to the present invention place it within the economic reach of most laboratories. Accordingly, the ability to measure fluorescence lifetimes using a multiple frequency phase-modulation technique no longer requires expensive apparatus employing complex and expensive methods. The basic apparatus according to a specific embodiment of the present invention comprises an optical bench, a lock-in amplifier, two bias tees, a blue light emitting diode (LED), a reference standard, a filter and a photomultiplier tube and has a component cost of less than US $10,000. Additionally, sample holders such as cuvettes, reaction chambers and flow cells can also be used. Similarly, photodiodes can be used in lieu of the photomultiplier tube.

The method of the present invention comprises the steps of (i) providing an AC reference signal; (ii) providing a DC bias signal; (iii) biasing the AC reference signal with the DC bias signal to produce a biased AC input signal; (iv) modulating a light source at a frequency of said biased AC input signal to produce modulated exciting light having a wavelength capable of exciting a photoluminescent species; (v) disposing a photoluminescent species in a sample holder; (vi) detecting modulated light emission from the photoluminescent species and producing a modulated electrical emission signal; (vii) processing the modulated electrical emission signal to obtain values indicative of the photoluminescent lifetime of the photoluminescent species.

It is another object of the present invention to provide a phase-modulation fluorometer which lends itself to portability and field use. It is a further object of the present invention to provide for use with fiber optics, making the phase-modulation fluorometer ideal for use with fluorescence lifetime based sensors. It is a further object of the present invention that it is portable, consumes little power, and is easily configured for use with fiber optics, making it ideal for field use with fluorescent lifetime based sensors.

In a preferred specific embodiment of the present invention employing heterodyning, a lock-in amplifier provides an AC reference signal and a DC bias signal. A bias tee is used to bias the AC reference signal against the DC bias signal producing a biased AC input signal. An output of the bias tee or the biased AC input signal is used to modulate a blue light emitting diode (LED) A modulated radiant output of the LED is used to excite a photoluminescent species that has been disposed in a sample holder. A modulated light emission from the photoluminescent species in the sample holder is detected by a photomultiplier tube producing a modulated electrical emission signal. A second bias tee is used to split the modulated electrical emission signal into its AC and DC component signals. The DC component is measured, and the AC component output is mixed with an AC reference signal whereby the phase and amplitude information are shifted to a lower frequency signal. The above lock-in amplifier is also used to sample, filter, apply offsets and analyze the lower frequency signal to obtain a DC value wherein the DC value is indicative of the value(s) of the photoluminescent lifetime(s) of the photoluminescent species that was disposed in the sample holder. No external signal processing or heterodyning is required of this lock-in amplifier based system.

In an alternative specific embodiment employing homodyning, after splitting the modulated electrical emission signal into its AC and DC component signals and measuring the DC component, the AC component is mixed with AC reference signals and the resulting signal is filtered and analyzed whereby the phase and amplitude information are expressed as two DC values that are indicative of the value(s) of the fluorescence lifetime(s) of a photoluminescent species.

In a further alternative specific embodiment employing direct sampling, after splitting the modulated electrical emission signal into its AC and DC component signals and measuring the DC component, the AC component is filtered, sampled and analyzed whereby the phase and amplitude information are expressed as two DC values that are indicative of the value(s) of the fluorescence lifetime(s) of a photoluminescent species.

It is expressly noted herein that the values obtained directly by the apparatus and methods of the present invention are not the lifetime(s) themselves and that these values require further computer analysis to interpret these values to thereby obtain the actual lifetime(s).

In yet another specific embodiment of the present invention involving heterodyning, the system further comprises a bifurcated fiber optic bundle having two proximal arms and a common end optically coupled to a porous fiber, solid or gel matrix (hereinafter a "sensor patch") containing one or more photoluminescent species. In this embodiment, a distal end of one of the proximal arms is optically coupled to a modulated light source; a distal end of the other proximal arm is optically coupled to a detector; and a common end of the bifurcated fiber optic containing the sensor patch is either disposed in a sample holder or optically coupled to the sample holder. The method of this alternative specific embodiment comprises the steps of (i) generating an AC reference signal; (ii) generating a DC bias signal; (iii) biasing the AC reference signal with the DC bias signal to produce a biased AC input signal; (iv) modulating a light source at a frequency of said biased AC input signal to produce modulated exciting light having a wavelength capable of exciting a photoluminescent species; (v) optically coupling a distal end of a first proximal arm of a bifurcated fiber optic to the modulated light source; (vi) disposing a common end of the bifurcated fiber optic which has at least one photoluminescent species disposed in a sensor patch on its end into a sample holder or optically coupling the common end of the bifurcated fiber optic to the sample holder; (vii) disposing an analyte or sample of interest into the sample holder or introducing a flow carrying the analyte or sample of interest into the sample holder; (viii) exciting the photoluminescent species with the modulated light source light; (ix) transmitting the modulated source light through the bifurcated fiber optic from the distal end of the proximal arm optically coupled to the modulated light source to the common end of the fiber optic to produce a corresponding emission from the photoluminescent species disposed on the common end of the fiber optic; (x) transmitting the modulated emission from the photoluminescent species disposed on the common end of the fiber optic to the distal end of a second proximal arm of the fiber optic; (xi) optically coupling a distal end of the remaining proximal arm of the bifurcated fiber optic to a detector; (xii) detecting the emission from the distal end of the remaining proximal arm of the bifurcated fiber optic, producing a modulated emission signal; (xiii) splitting the modulated emission signal into its AC and DC components, measuring the DC component, and mixing the AC component with an AC reference signal whereby the phase and amplitude information are shifted to a lower frequency; and (xiv) sampling, filtering, applying offsets and analyzing said lower frequency signal to obtain a DC value wherein the DC value is indicative of a value of the photoluminescent lifetime of the photoluminescent species.

The use of the bifurcated optic bundle in the alternative specific embodiment obviates the need for the optical bench such as described in the first preferred specific embodiment involving heterodyning. Further, the bifurcated optic bundle optically couples both the modulated light source and the detector with a photoluminescent species disposed at the common end of the optic bundle. Signal processing is performed as described above.

In yet a further alternative specific embodiment again using the bifurcated fiber optic and further employing homodyning, and as previously described, after splitting the modulated electrical emission signal into its AC and DC component signals and measuring the DC component, the AC component is mixed with AC reference signals and the resulting signal is filtered and analyzed whereby the phase and amplitude information are expressed as two DC values that are indicative of the value(s) of the fluorescence lifetime(s) of a photoluminescent species.

In yet a further alternative specific embodiment again using the bifurcated fiber optic and further employing direct sampling, and as previously described, after splitting the modulated electrical emission signal into its AC and DC component signals and measuring the DC component, the AC component is filtered, sampled and analyzed whereby the phase and amplitude information are expressed as two DC values that are indicative of the value(s) of the fluorescence lifetime(s) of a photoluminescent species.

In another specific alternative embodiment using the bifurcated fiber optic, the photoluminescent species is immobilized on the common end of the fiber optic.

In a further specific alternative embodiment using the bifurcated fiber optic, the sensor patch is eliminated and one or more photoluminescent species are disposed in the sample holder with an analyte or sample of interest, or a flow carrying the photoluminescent species and the analyte or sample of interest is introduced into the sample holder.

In a further specific embodiment, the entire lock-in amplifier based system can be controlled by any standard personal computer through a GPIB, USB, serial or similar connection on the lock-in amplifier.

In a further specific embodiment the present invention is battery operated and portable making it ideal for use with photoluminescent lifetime based sensors.

BRIEF DESCRIPTION OF THE DRAWINGS

The present invention will become better understood by reference to the following drawings, wherein.

DETAILED DESCRIPTION OF THE PREFERRED EMBODIMENT

General

Figure 1:
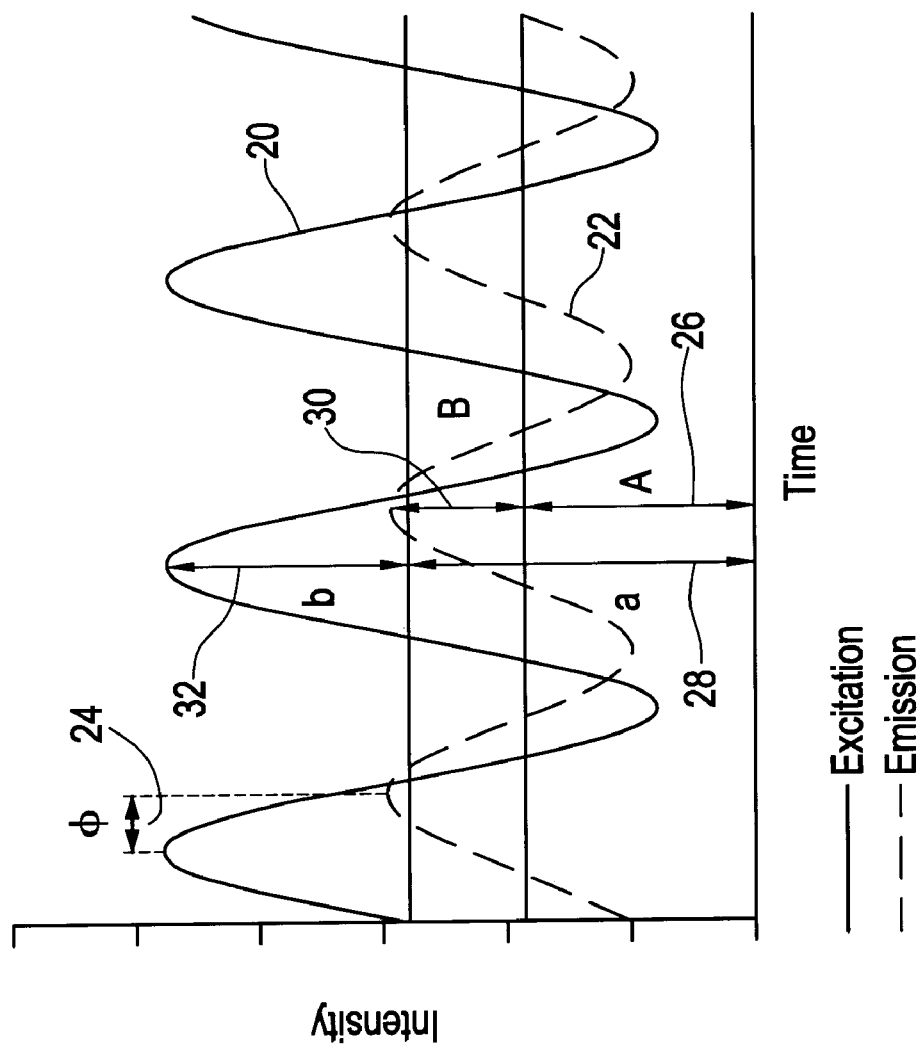
FIG. 1 is a prior art graph of simulated plots of phase angle, $\phi$, and modulation, m, as a function of time, between an excitation light source and a photoluminescent emission.

The foregoing aspects and many of the attendant advantages of the present invention will become more readily appreciated to those skilled in the art as the same becomes better understood by reference to the following detailed description, when taken in conjunction with the accompanying drawings, wherein like reference characters designate like parts throughout the several views.

Referring to FIG. 1, upon the pulsing or sinusoidal modulation of a conventional excitation light (not shown) using conventional frequency domain or phase modulation methods, the resulting light intensity is shown by waveform 20. When the light output excites a fluorophore sample the resulting fluorescence emission waveform 22 is at the same circular frequency as the excitation light waveform 20. However, due to the finite duration of the fluorophore's excited state, the emitted fluorescence has the same circular frequency as excitation light waveform 20 but lags excitation light waveform 20 in phase by an angle φ, shown at 24. In addition, the depth of modulation compared to the excitation is also reduced. A demodulation factor, m, is given by equation 1 as follows:

$$m=(B/A)/(b/a) \qquad (1);$$

where "A" is the average value of the emitted fluorescence and is shown at 26; "a" is the average value of the excitation light and is shown at 28; "B" is the amplitude of the peak emission above the average value of the emitted fluorescence 26 and is shown at 30; and "b" is the amplitude of the peak excitation above the average value of the excitation light 28 and is shown at 32.

Photoluminescent or more particularly fluorescent compounds emit light following exposure to light of certain wavelengths. The intensity of the emitted light decreases gradually after the exciting light is removed. The lifetime of a photoluminescent compound can be defined as the time required for the intensity of the emitted light to decay to 1/e of its initial value. Alternatively, the lifetime of a photoluminescent compound can be defined in terms of the average amount of time a photoluminescent compound spends in the excited state. In the case of fluorescence, emission arises from a quantum-mechanically "allowed" transition between molecular states of the same multiplicity; whereas phosphorescent emissions arise from a quantum-mechanically "forbidden" transition. Typically, fluorescence lifetimes are on the order of 10 nsec; whereas typical phosphorescence lifetimes range from milliseconds to seconds, depending on the importance of other processes which similarly lead to the deactivation of the excited state. See, e.g., Lakowicz, J. R. "Principles of Fluorescence Spectroscopy", Plenum Press, New York (1983).

Light Source and Fluorophore Selection

Figure 2:
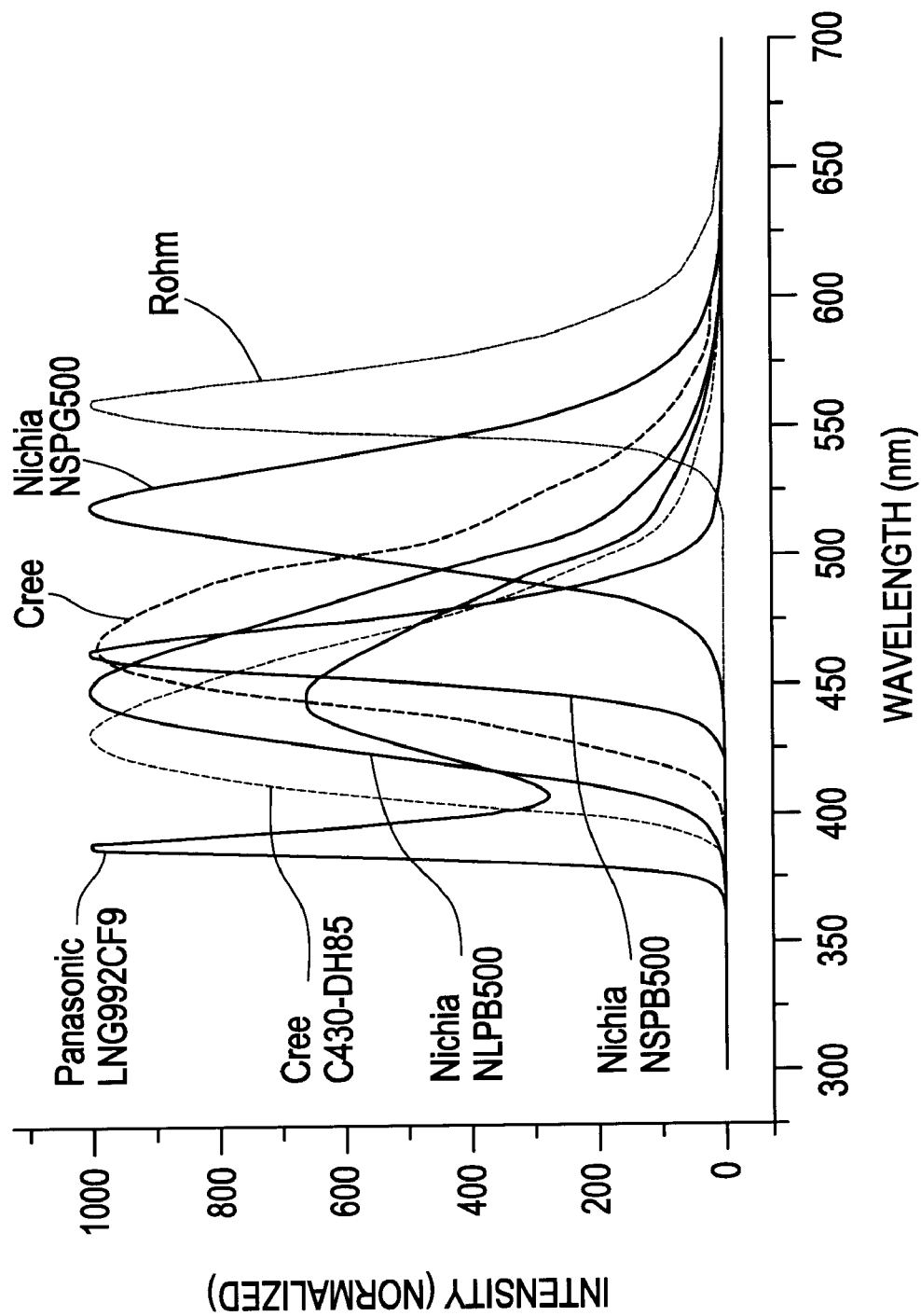
FIG. 2 is a prior art graph of the spectral outputs of commercially available LEDs which represent the current range of known low cost visible excitation sources.

To minimize component costs, in a preferred embodiment of the present invention an LED is used as an excitation source. Alternatively, depending upon the application, a flash lamp, a laser diode, or a pulsed laser can also be used. The spectral outputs of several commercially available LEDs were measured by directing the output from each LED into an S10 monochromator with 4 nm slits, and measuring the intensity with a photomultiplier tube at 2 nm intervals. The spectral outputs from a number of commercially available LEDs is given in FIG. 2. As is clearly apparent from FIG. 2, the entire visible and some of the UV region of the spectrum is covered, enabling the use of several commercially available fluorophores. In addition, many of these LEDs are easily modulated to several MHz (Sipior et al., 1996). Recently a Panasonic LED has become available that can generate light modulated in excess of 200 MHz. In experiments conducted using the present invention a blue LED excitation source (Nichia Chemical Industries, NSPB500, Lancaster, Pa.) was used.

All fluorophores were purchased from Aldrich (Milwaukee, Wis.) and used without further purification. Fluorescein Disodium Salt was dissolved in a 50 mM MES buffer at pH 5.5. Rhodamine B was dissolved in deionized water. Tris (2,2'-Bipyridine)-Ruthenium (II) Chloride ([Ru (bPY)$_3$]$^{2+}$)was dissolved in deionized water, with no attempt made to remove dissolved oxygen. Five percent (5%) Ludox (DuPont, Wilmington, Del.) in deionized water was used as the reference in all examples where system performance was compared to an ISS research grade phase fluorometer (ISS, Champaign, Ill.).

Preferred Embodiments

Figure 3:
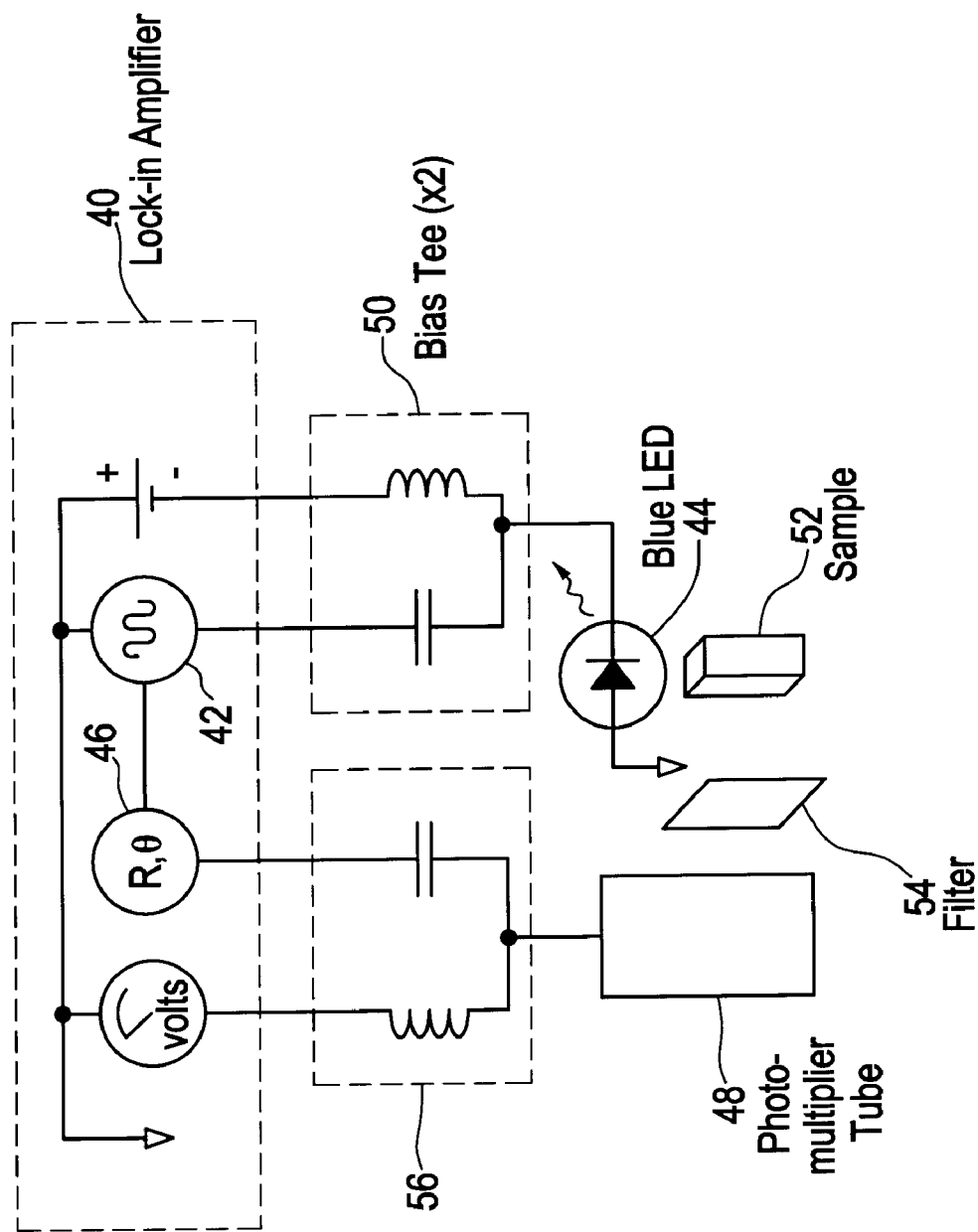
FIG. 3 is a schematic electrical block diagram of a preferred embodiment of a basic lock-in amplifier multiple frequency phase-modulation fluorometer of the present invention.

FIG. 3 illustrates a first preferred embodiment of the present invention. In a basic setup, a main component is a conventional hybrid analog/digital lock-in amplifier 40 (such as currently produced by Stanford Research Systems, M/N SR844, Sunnyvale Calif.). Lock-in amplifier 40 generates a wave form 42 that is fed to an input of a first bias tee 50 whose output modulates a blue LED 44. Lock-in amplifier 40 also generates an internal waveform 46 that is used to down shift phase information from a photomultiplier tube 48. Internal waveform 46 is chopped by 2–12 kHz as compared to waveform 42 used to modulate blue LED 44. Blue LED 44 is located so that its light emissions excite sample 52. Sample 52 produces light emissions, in turn, that are filtered by filter 54. The light emissions from sample 54 are detected and converted to an electrical signal by photomultiplier tube 48 (Hamamatsu, R928, Bridgewater, N.J.) and an output signal of photomultiplier tube 48 is electrically connected to a common end of a second Bias Tee 56 which acts as a diplexer, splitting the output signal into its AC and DC components while minimizing signal loss. The AC component is then fed into a signal input of lock-in amplifier 40 and the DC component is measured by an analog-to-digital converter that is built into lock-in amplifier 40. After down-shifting phase information from photomultiplier tube 48, lock-in amplifier 40 samples the resulting signal at 48–96 kHz and feeds this signal to a digital signal processor (DSP) for additional filtering, application of offsets, and conversion to DC. This arrangement allows lock-in amplifier 40 to operate at much higher frequencies than the DSP can normally handle and yet retains the advantages of digital processing. These advantages include the elimination of problems associated with DC offset and allow the selection of a wide range of time constant filtering (100 µs–30 ks) to change the bandwidth of lock-in amplifier 40. Further, lock-in amplifier 40 has two digital-to-analog converters, one of which is used to supply the DC bias for blue LED 44, and two analog-to-digital converters, one of which is used to measure the DC component of photomultiplier tube 48 output. Coherent pickup from external components can be minimized by using microwave grade cables for all lock-in amplifier connections.

In a preferred embodiment for phase-modulation measurements, blue LED 44 is a blue LED excitation source and is directly modulated by a 1 v p-p square wave output of lock-in amplifier 40. Blue LED 44 is biased at 2.9 v through Bias Tee 50 (Picosecond Pulse Labs, 5590, Boulder, Colo.).

Figure 11:
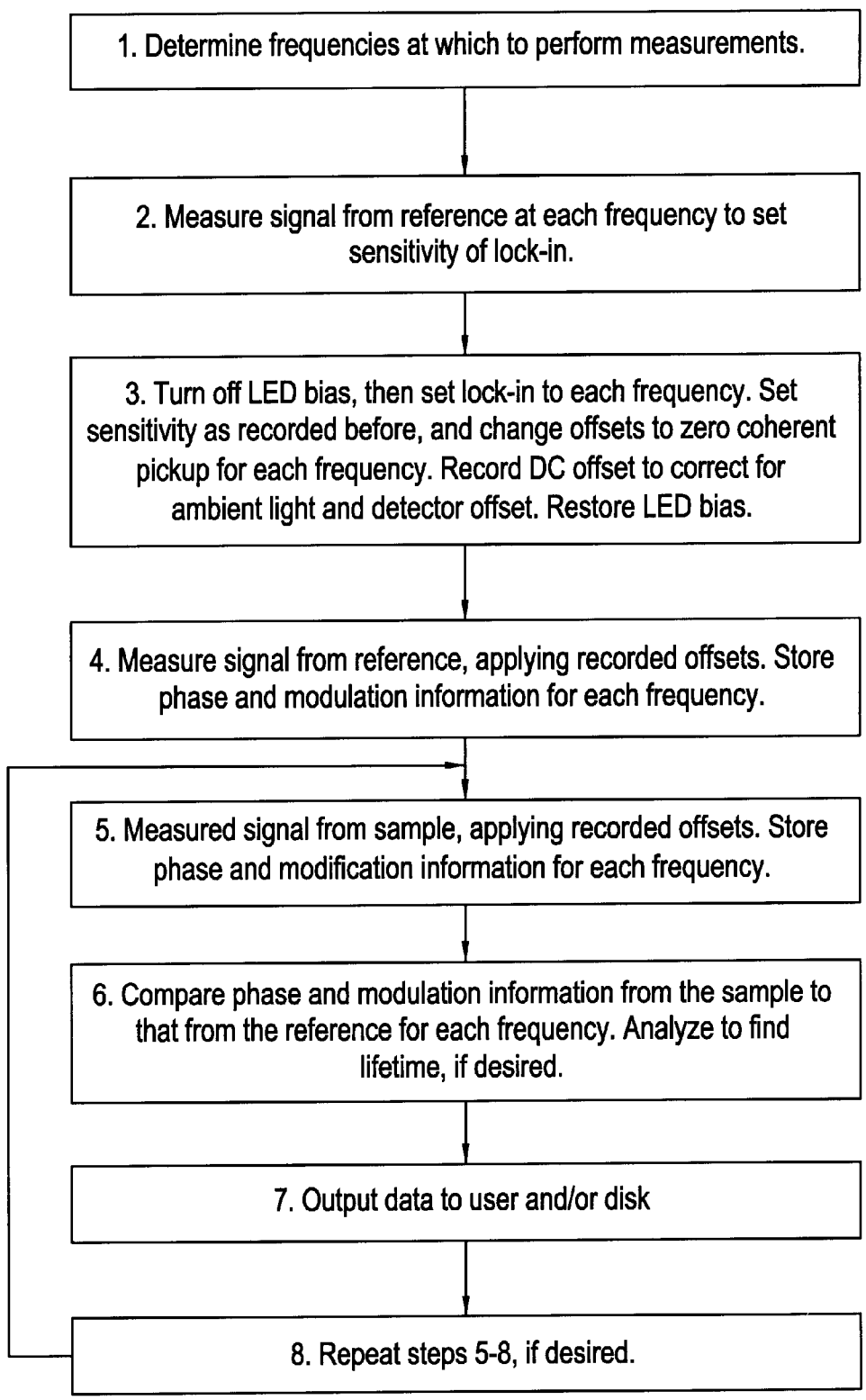
FIG. 11 is a functional block diagram of a simple interface program for a personal computer that provide for automated control of a lock-in amplifier in the set-up of the present invention.

Lock-in amplifier 40 is also equipped with an RS-232 port and a GPIB port, either of which can be used to control the features of lock-in amplifier 40 by a personal computer (PC) (not shown). Referring now to FIG. 11, a simple interface program can be written to provide for the automated control of lock-in amplifier 40 from the PC. In a preferred embodiment the interface program was written in Microsoft Visual Basic. Other programing languages can also be used. The program can be used to set lock-in amplifier 40 sensitivity, correct for coherent pick-up, measurement of the reference and measurement of the sample. This automation is very useful when measurements are taken at multiple frequencies. Variations of this program can also be developed to periodically take measurements for long-term stability experiments.

In the preferred embodiment at high frequencies, low signal level limits the performance of the basic lock-in amplifier 40 setup. Specifically, performance of lock-in amplifier 40 is degraded by coherent pickup in the signal path at higher frequencies (User's Manual, Model SR844 RF lock-in amplifier. Stanford Research Systems. Rev. 2.3, pp. 2.20–2.21, 1997). The coherent pickup is negligible at less than 50 MHz, but comparable to signal voltage at 100 MHz. Further, using a light source that can be modulated at higher frequencies, such as a laser diode improves high frequency measurements. Alternatively, the power of the AC signal sent to blue LED 44 can be increased to make it modulate more efficiently. Blue LED 44 used in the basic setup can have a modulation of over 100% at low frequencies if sufficient power is used, but the 1 v p-p output of lock-in amplifier 40 only provides a modulation of about 75%.

Figure 4:
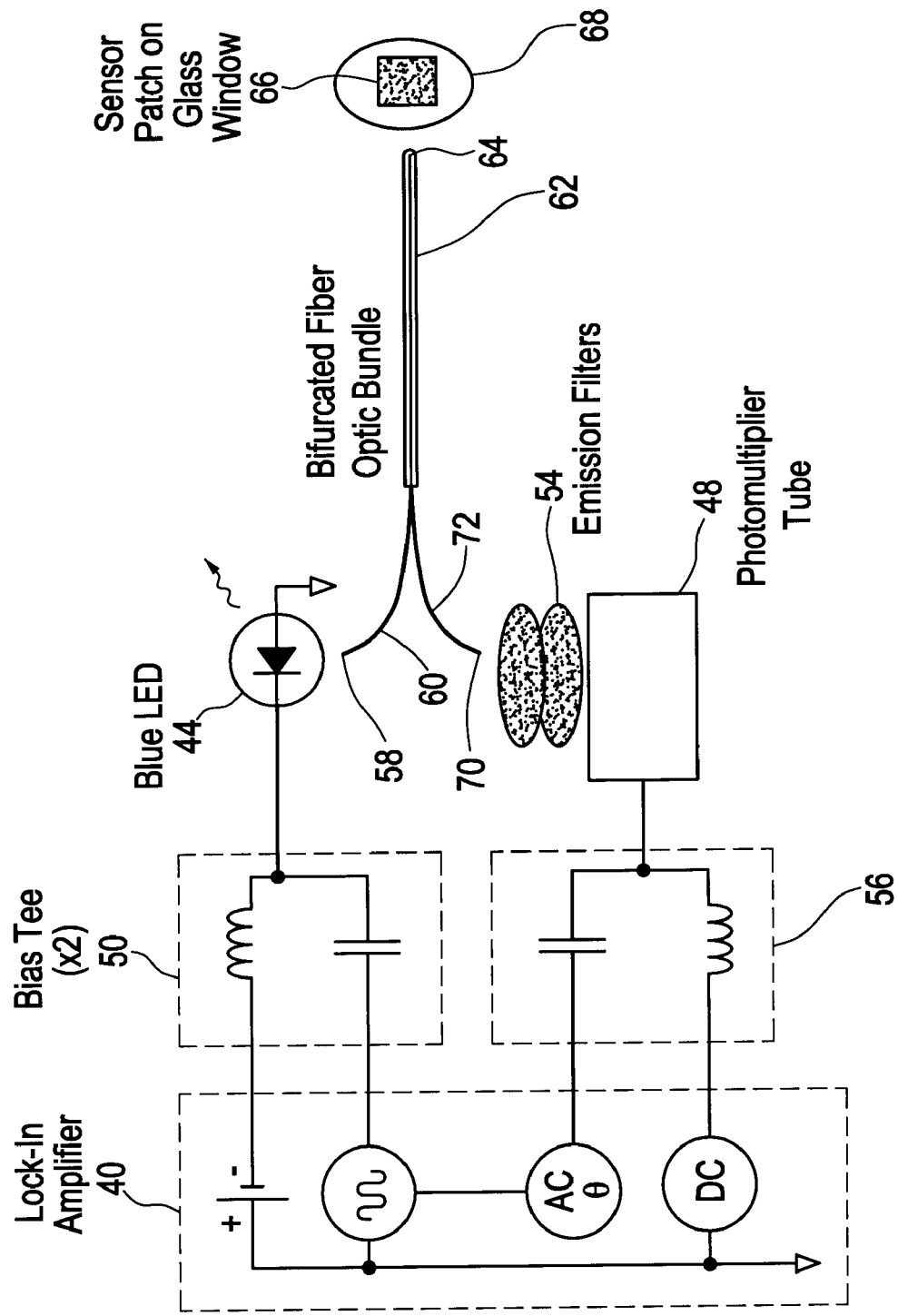
FIG. 4 is a schematic electrical block diagram of an alternative embodiment of the lock-in amplifier based multiple frequency phase-modulation fluorometer of the present invention configured for use with a bifurcated fiber optic bundle.

FIG. 4 is an alternative embodiment of the invention of FIG. 3. A description of the portions of this embodiment which are common to FIG. 3 are not repeated herein and the description applicable thereto, as set forth with respect to FIG. 3, is incorporated herein by reference. In the embodiment of FIG. 4, blue LED 44 is optically coupled to a distal end 58 of a first proximal arms 60 of a fiber-optic bundle 62. Fiber optic bundle 62 has a common end 64, and another distal end 70 disposed at the end of a second proximal arm 72. Sensor patch 66 is optically coupled to common end 64 of fiber-optic bundle 62. Alternatively, sensor patch 66 can be disposed in sample holder 68, which is optically coupled to fiber optic bundle 62. Distal end 70 of second proximal arm 72 is optically coupled through filter 54 to photomultiplier tube 48.

Figure 5:
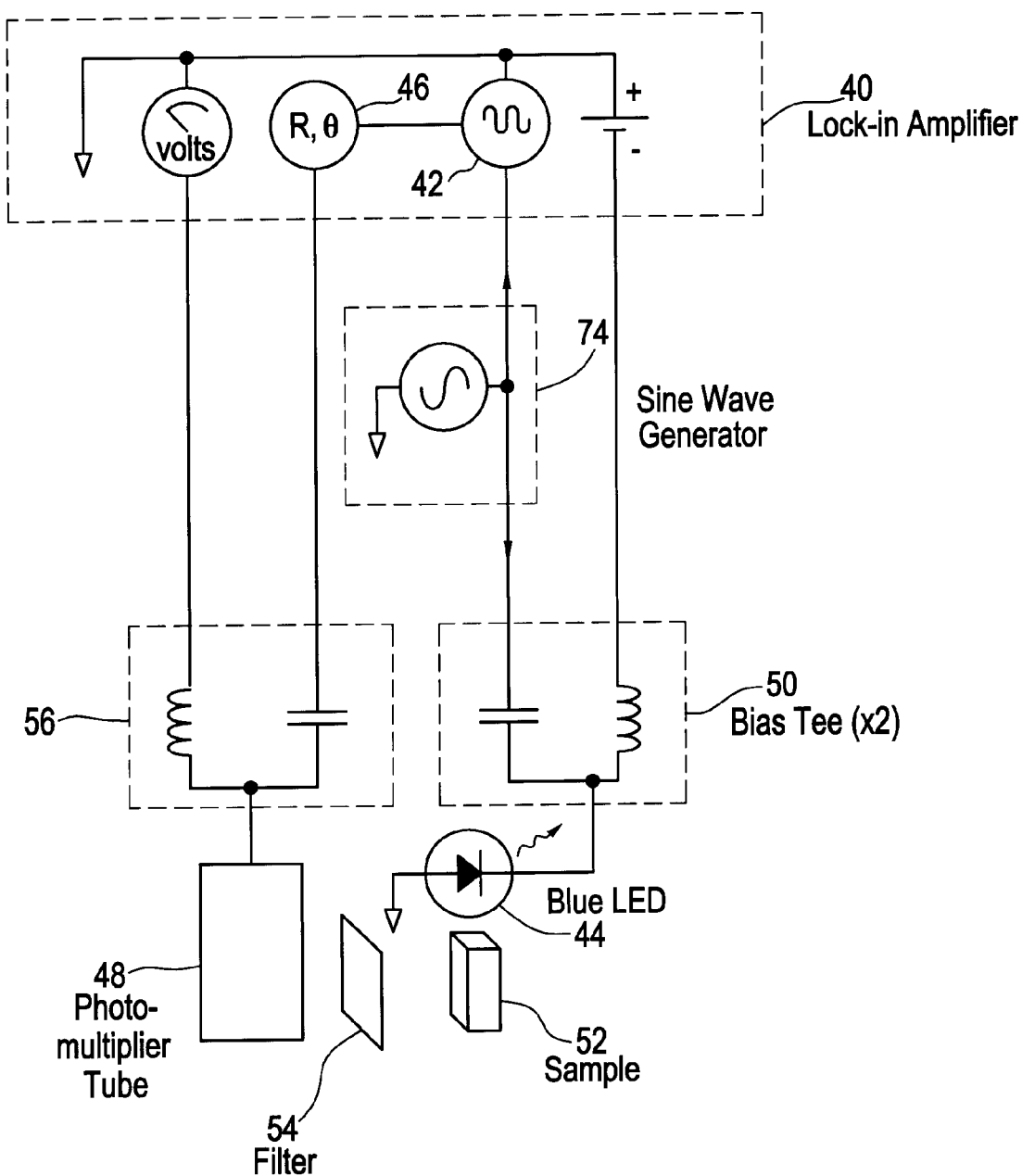
FIG. 5 is a schematic electrical block diagram of a further alternative embodiment of the basic lock-in amplifier based multiple frequency phase-modulation fluorometer of the present invention configured for use with an external frequency generator.

FIG. 5 is a further alternative embodiment of the invention of FIG. 3. As before, a description of the portions of this embodiment which are common to FIG. 3 are not repeated herein and the description applicable thereto, as set forth with respect to FIG. 3, is incorporated herein by reference. In the embodiment of FIG. 5 an external signal generator 74 (Marconi Instruments, 2022D, Allendale, N.J.) is connected to a junction point between lock-in amplifier 40 and bias tee 50. In contrast to lock-in amplifier 40 which provides a square wave AC output, signal generator 74 provides a sine wave output at a variable power level of up to +13 dBm. Alternative frequency generators can also provide various other wave forms including a sine wave and a square wave. An alternative lock-in amplifier 40 of the basic setup can provide sine wave outputs to obviate the need for external signal generator 74. In the modified configuration of FIG. 5, the AC square wave functions of lock-in amplifier 40 are not used. Again, the sample holder 68 was used as above for its convenient optics.

EXAMPLES

By way of example, and not by way of limitation, the foregoing aspects and many of the attendant advantages of the present invention will become more readily appreciated to those skilled in the art by the following examples and experimental results.

Example 1
Basic Lock-In Amplifier Setup

The basic lock-in amplifier setup as shown in FIG. 3 and described above was used to measure the fluorescence lifetime of a fluorescein stock solution. This setup included an ISS Koala sample compartment which provided a convenient and flexible way to switch between measuring a reference scattering solution and the sample. Further, the sample compartment is based on a standard right angle (90 degree) orientation between the excitation source and the emission detector. No filters were required in the excitation path due to the high intensity emission of the fluorophore solutions used and because blue LED 44 emitted almost no light at greater than 600 nm. For the emission path of the reference scattering solution, neutral density filters 54 were used to avoid saturating photomultiplier tube 48. For the emission path of the fluorophores, scattered excitation light was removed by an 600 nm long wave pass filter (Andover, 600 FH- 50S, Salem, N.H.). No reference detector was needed as the output of blue LED 44 remained stable.

The basic setup which uses the square wave AC output of lock-in amplifier 40 to modulate blue LED 44 is suitable for measuring fluorescent lifetimes on the order of a few nanoseconds. The lifetime of fluorescein was measured using the basic setup. For purposes of comparison, the lifetime of the same fluorescein stock solution was measured using an ISS research grade phase fluorometer (not shown) which is typical of most cross-correlation phase fluorometers (Gratton and Limkeman, 1983). The ISS used the same blue LED 44 for its excitation source as was used in the basic setup. However, blue LED 44 of the ISS is DC biased by a high precision current source (ILC Lightwave LDX-3412) (not shown), whereas the AC for blue LED 44 is provided by a high quality signal generator (Marconi 2022D) such as generator 74 shown in FIG. 5. The AC and DC signals are mixed by the same bias tee 50 used in the basic lock-in amplifier 40 setups shown in FIG. 3.

The major difference between the two setups is in the detector. In the ISS setup a second signal generator (not shown) is synchronized with the first one (not shown), but run at a slightly higher frequency. The output of this second signal generator is processed through a high power amplifier (not shown) and is used to modulate the potential between the last few dynodes inside photomultiplier tube 48. In brief, photomultiplier tube 48 of the ISS acts as a mixer, combining the frequency of the fluorescence emission which is the same as the frequency of the excitation source with the frequency of the second signal generator. Further, the phase and modulation information is sampled at the offset frequency which in this case was 400 Hz. After a simple low-pass filter is applied to remove the high frequency components from the mixing operation, simple electronics can be used to measure the phase and modulation.

Figure 6A:
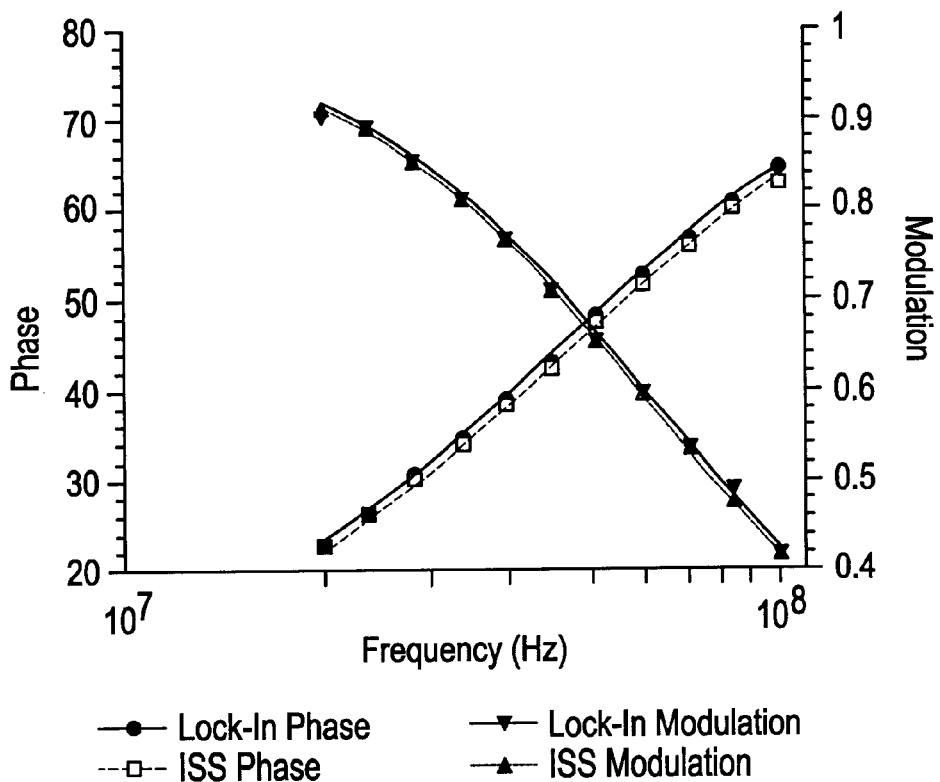
FIG. 6A is a graph that depicts phase and modulation data for the basic lock-in amplifier setup and for an ISS research grade cross-correlation fluorometer showing the measured data and the best fits to a monoexponential decay law for a solution of fluorescein, dissolved in water buffered at pH 5.5.
Figure 6B:
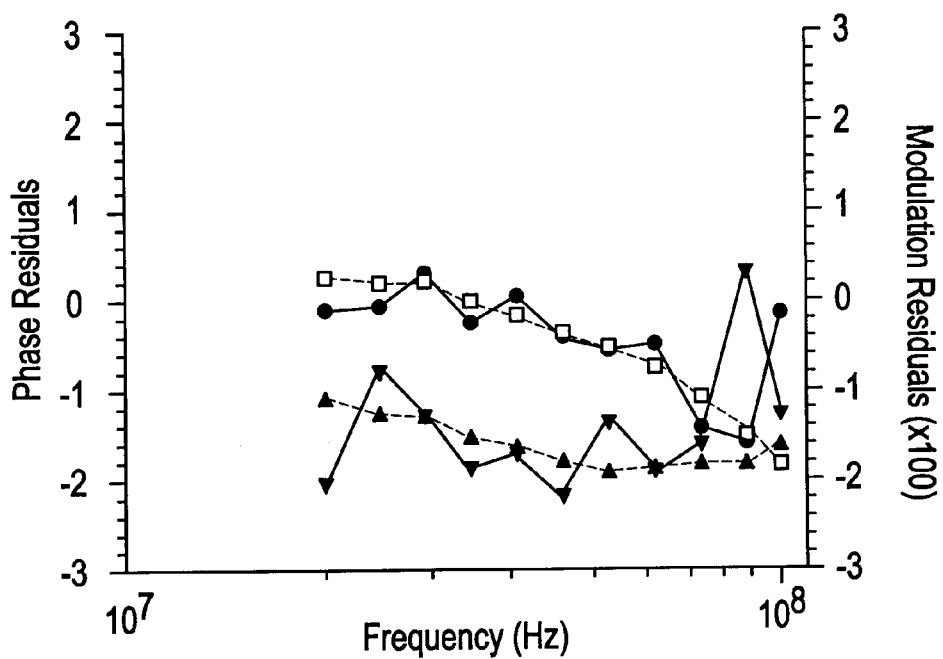
FIG. 6B is a graph that depicts phase and modulation data for the basic lock-in amplifier setup and for an ISS research grade cross-correlation fluorometer showing the residuals of the fits of FIG. 6A.

The basic lock-in amplifier setup accurately matched the data from the ISS research grade phase fluorometer to upwards of 80 to 100 MHz. As expected, at high frequencies, modulation results were more accurate than phase data. Least squares curve fitting of the experimental results for the basic lock-in amplifier setup provided a measure of the lifetime for fluorescein of 3.36 ns, while least squares curve fitting for the ISS data fit a lifetime of 3.31 ns. FIGS. 6A and 6B depict phase and modulation data for both the basic lock-in amplifier setup and that for the ISS research grade cross-correlation fluorometer for the solution of fluorescein, dissolved in water buffered at pH 5.5. FIG. 6A shows the measured data and the best fits to a monoexponential decay law. The residuals of these fits are shown in FIG. 6B. Both lifetimes measurements appear quite reasonable given the reported lifetime of fluorescein is about 3.4 ns (Sipior et al., 1996). The basic lock-in amplifier setup and the ISS were also used to measure the fluorescence lifetime of Rhodamine B (data not shown). The lock-in amplifier fit a lifetime of 1.64 ns, which compares favorably to the ISS fit of 1.65 ns and the previously reported lifetime of 1.68 ns (Gryczynski et al., 1997).

Example 2
Low Frequency Lock-In Amplifier Setup

Although in the preferred embodiment lock-in amplifier 40 can measure up to 200 MHz, its applications are limited as it produces square waves. This does not present a problem for measurements at high frequencies because of the 200 MHz bandwidth of lock-in amplifier 40 and the 58 MHz bandwidth of blue LED 44. However, at frequencies below 20 MHz, the high order harmonics of the square wave become an important factor as the phase and modulation measurements reflect not just the fluorophore's response at the fundamental frequency but that of the harmonics as well. To solve this problem the basic lock-in amplifier setup was modified as shown in the alternative embodiment of FIG. 5.

Figure 7B:
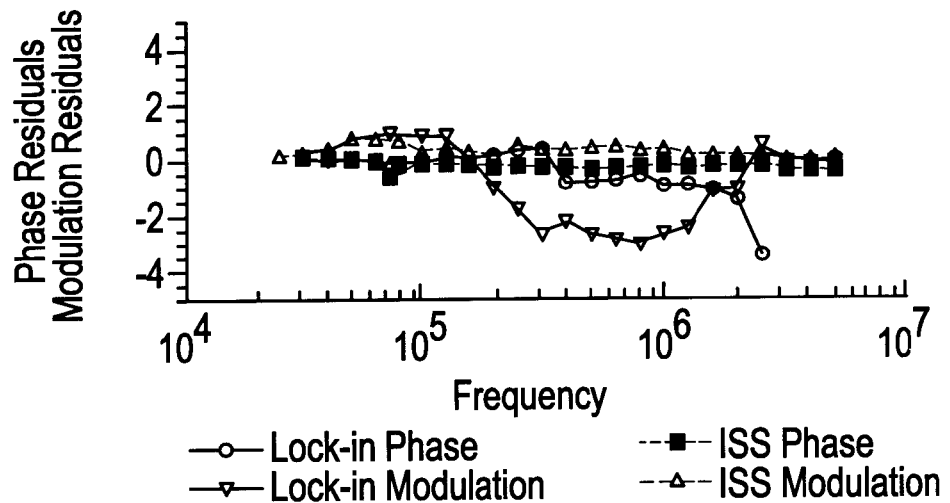
FIG. 7B is a graph that depicts phase and modulation data for the basic lock-in amplifier setup and for an ISS research grade cross-correlation fluorometer showing the residuals of the fits of FIG. 7A.
Figure 7A:
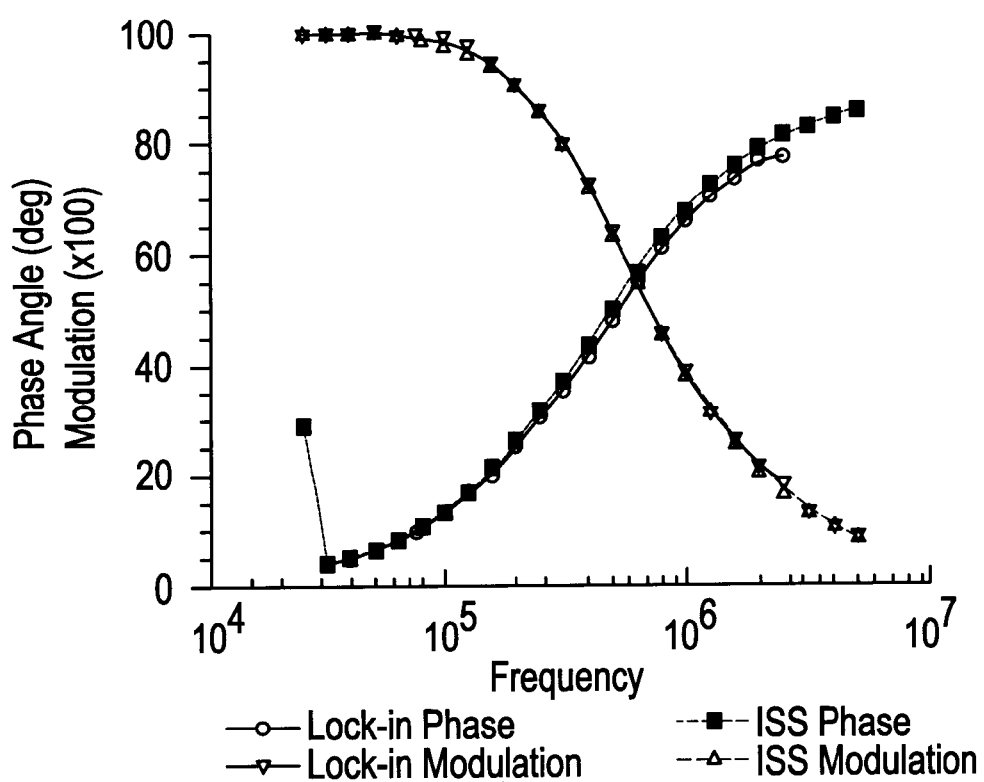
FIG. 7A is a graph that depicts phase and modulation data for the modified lock-in amplifier setup and that for an ISS research grade cross-correlation phase fluorometer showing the measured data and the best fits to a monoexponential decay law for a ruthenium complex dissolved in deionized water (Tris (2,2'-Bipyridine)-Ruthenium (II) Chloride ([Ru(bpy)$_3$]$^{2+}$).

The modified lock-in amplifier setup accurately matched the data from the ISS at the lower modulation frequencies used to measure the lifetime of the ruthenium complex (Tris (2,2'-Bipyridine)-Ruthenium (II) Chloride ($[Ru(bpy)_3]^{2+}$) ) . The phase and modulation data are provided in FIGS. 7A and 7 B. The lock-in amplifier data fits a lifetime of 361 ns, as compared with the ISS result of 395 ns. The widely inaccurate phase measurement by the ISS at 25 kHz is due to a bandwidth limitation of the high-power amplifier required to modulate the photomultiplier tube. As the lock-in amplifier setup does not modulate the photomultiplier tube at all, it avoids this limitation.

Example 3
Carbon Dioxide Sensor

Figure 8:
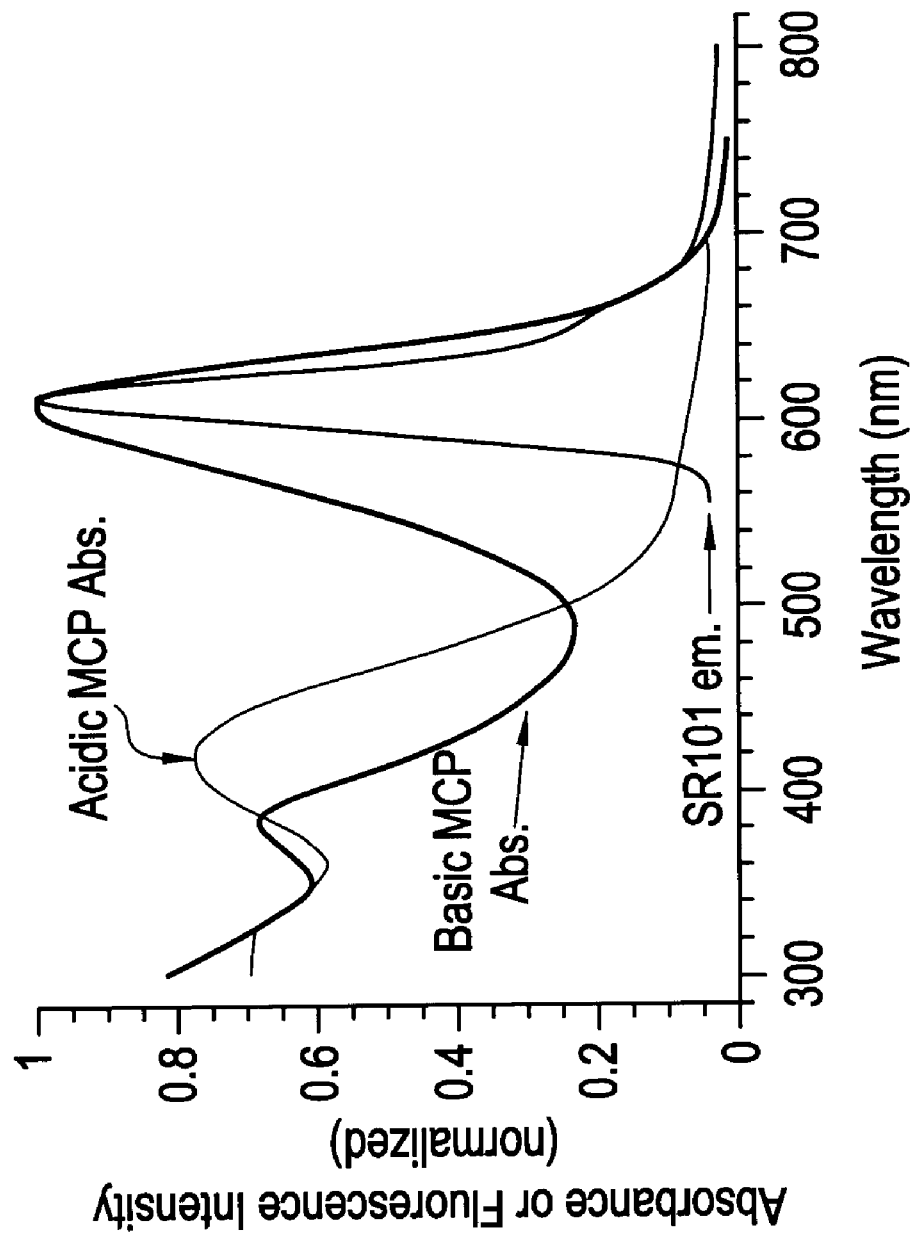
FIG. 8 is a prior art graph that shows the spectral characteristics of sulforhodamine 101 (SR 101); and m-cresol purple (MCP) in both a basic form and an acidic form, in a sensor patch for carbon dioxide.

Referring again to FIG. 4, a fiber optic configuration of the set up of lock-in amplifier 40 was used to demonstrate system performance using a carbon dioxide sensor. This is the least expensive configuration and is well suited for remote sensing applications. A conventional sensor patch 66 was constructed for dissolved carbon dioxide as described by Chang et al. (1998). Sensor patch 66 is based on fluorescence resonance energy transfer (FRET) from sulforhodamine 101 hydrate (Aldrich, Milwaukee, Wis.) to the pH sensitive dye m-cresol purple (Aldrich, Milwaukee, Wis.). Sensor patch 66 contains the dyes and a quaternary amine ion pairing agent within a silicone film. An additional layer of white silicone is added to prevent the detection of fluorescence from contaminants in the medium. In brief, carbon dioxide gas permeates the silicone layers and reacts with the water molecules associated with the amine to form carbonic acid. Next, the carbonic acid protonates the pH sensitive dye, changing the absorbance spectrum. The spectra for the sulforhodamine and the protonated forms of m-cresol purple are shown in FIG. 8. The basic or deprotonated form of m-cresol purple absorbs strongly at 600 nm, so more FRET occurs, reducing the fluorescence lifetime. The acid form, however, does not absorb strongly at 600 nm, so less FRET occurs, and the fluorescence lifetime approaches the theoretical lifetime of sulforhodamine (about 4 ns) at very high levels of carbon dioxide. Sensor patch 66 was used to monitor dissolved carbon dioxide levels in an aerobic batch fermentation of E. coli JM105. The bacteria were grown at 35° C. with a constant flow rate of 1 VVM of air entering the bioreactor. Sensor patch 66 was placed inside the reactor on the window of a specially modified 25 mm probe. Bifurcated fiber optic bundle 62 was outside the reactor, with common end 64 aimed through a window of sample holder 68 at sensor patch 66. The only part of the fiber optic lock-in amplifier system that was in contact with the fermentation culture was sensor patch 66. Phase and modulation were measured by lock-in amplifier 40 at 74 MHz which provided the best signal-to-noise ratio.

Figure 9:
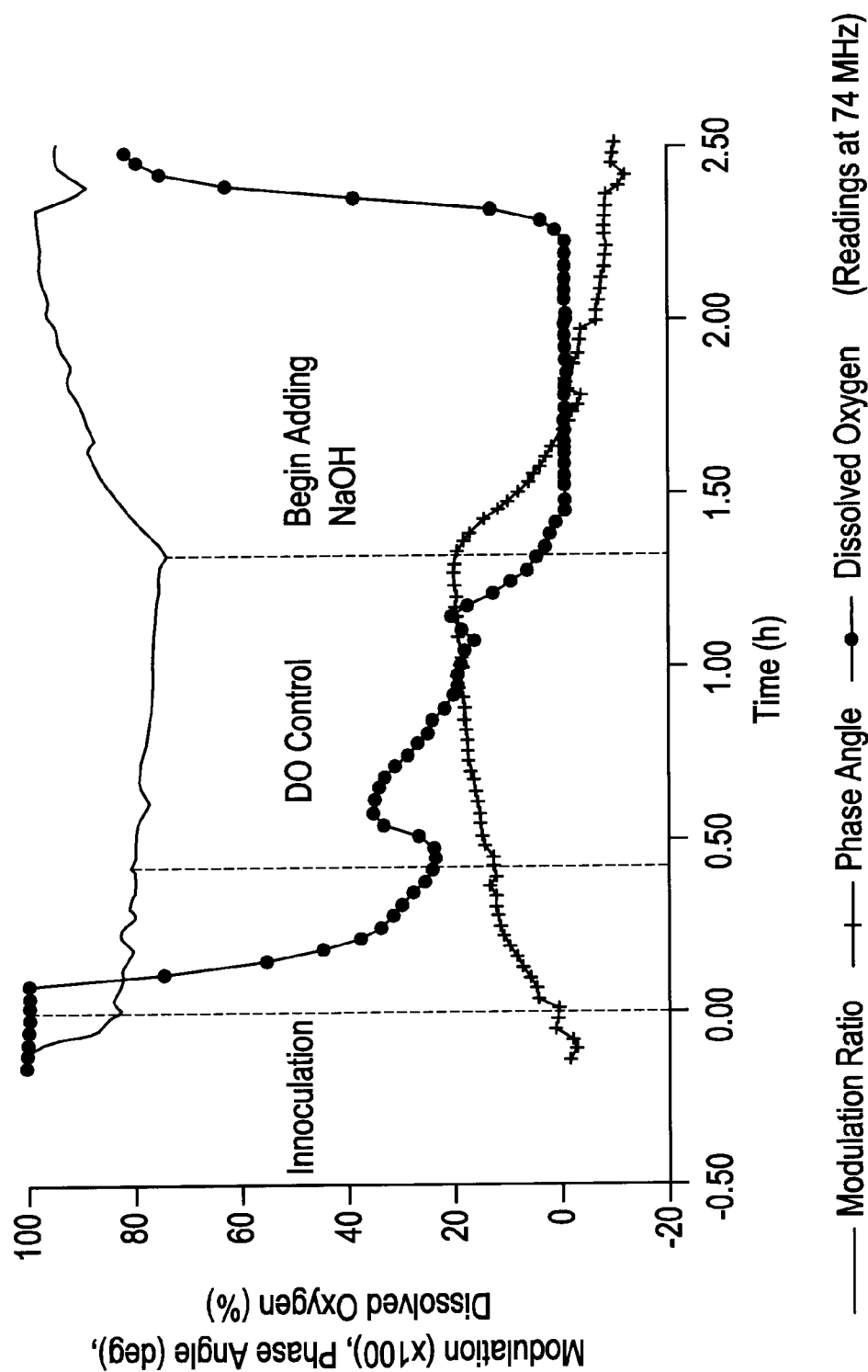
FIG. 9 is a graph that shows the phase angle and modulation measurements from an online dissolved carbon dioxide sensor which along with a Clark oxygen electrode was used to monitor the progress of an *E. coli* fermentation.

Measurements from the *E. coli* fermentation are shown in FIG. 9. Phase angle and modulation measurements are from the carbon dioxide sensor, and dissolved oxygen measurements are from a standard Clark oxygen electrode. Before the bacterial culture was inoculated into the reactor, the reactor was air equilibrated (essentially no carbon dioxide) with reference measurements being made for phase angle and modulation. The culture was then inoculated at time 0, with carbon dioxide levels rapidly rising, as shown by a decrease in modulation and an increase in phase angle. At time 0.5 h, a dissolved oxygen control was enabled, increasing the agitation speed of the reactor in an attempt to keep dissolved oxygen at 30%. From time 1.4 h to about 2.4 h, 200 mL of 1 M NaOH was added gradually into the 1.3 L of fermentation broth. Initially, this lowers the amount of dissolved carbon dioxide by converting carbon dioxide into bicarbonate ions. At time 2.3 h, the broth became too basic for proper metabolism of the bacteria, so the dissolved oxygen rapidly increased due to cessation of microbial activity.

Performance of the sensor was evaluated by comparing the relative changes of the phase angle with the modulation factor. As both are independent measures and tracked each other reasonably well, system performance was deemed satisfactory. The sensor showed a maximum change of about 20 degrees of phase angle and about a 0.25 change in modulation, which both correspond to a carbon dioxide partial pressure of approximately 15 torr. Higher than expected noise in the phase and modulation measurements is attributed to the increased RF noise level created by the operation of the fermentor.

Example 4

System Stability and Precision

Figure 10:
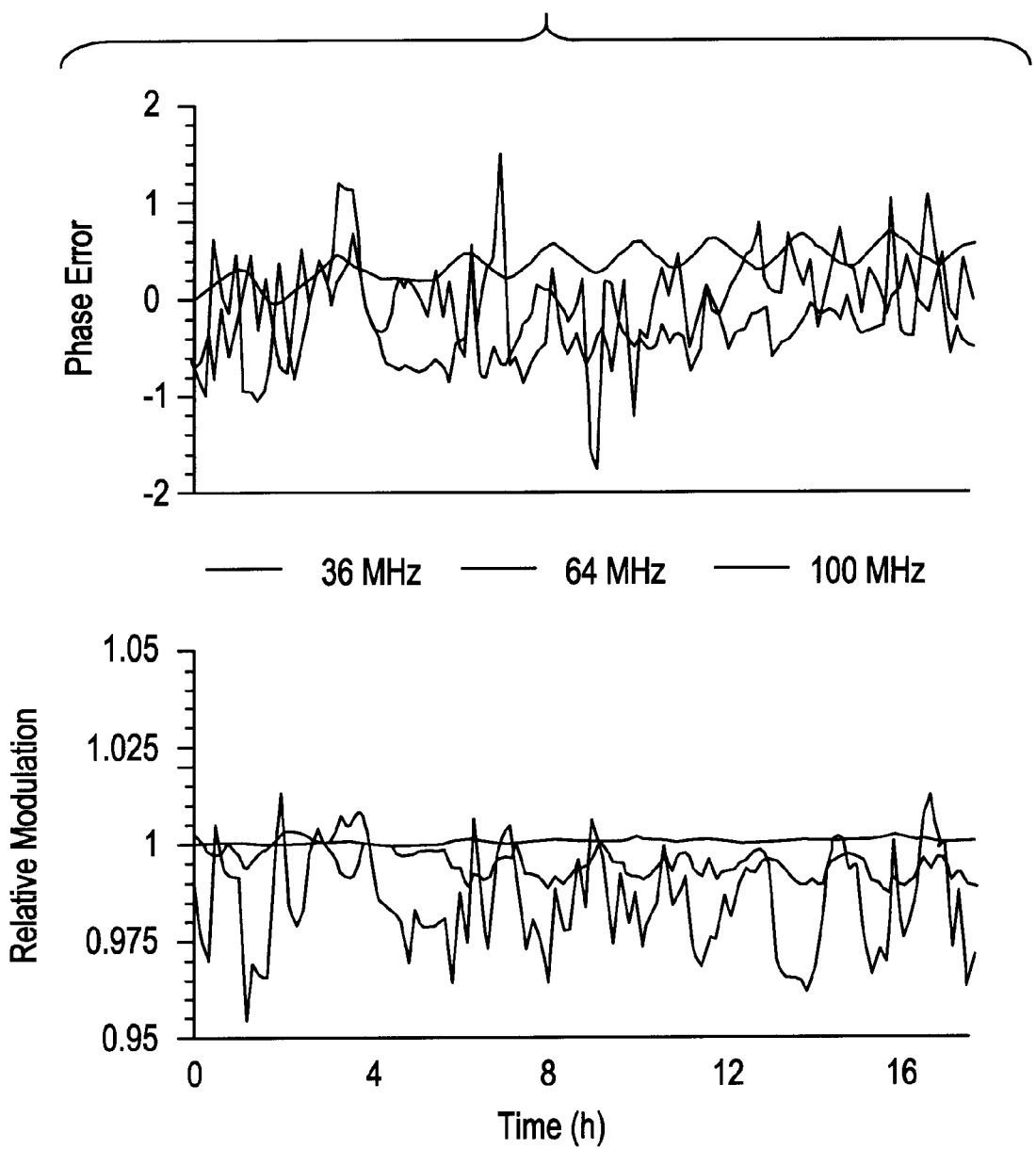
FIG. 10 is a graph, at each of several frequencies, that illustrates the stability of the lock-in amplifier based phase-modulation fluorometer of the present invention where Rhodamine B was measured, without using a lifetime reference, to show drift of the lock-in amplifier over 18 hours; and for which no drift would be reflected by a constant value of 1.000 for modulation (top graph) and 0.0 for phase angle (bottom graph) at all frequencies.

The fiber optic configuration was also used for long term stability testing of the system. For this purpose, a Rhodamine B sample was measured, and the drifts of the phase and modulation recorded. A representative run is shown in FIG. 10. The time scale represents how long it has been since the reference sample has been measured. Phase and modulation were measured at several frequencies without using a lifetime reference to show drift of the system over 18 hours. Results showed little or no drift in system performance. Long term stability of the lock-in amplifier system was excellent. For sensing applications, system re-calibration on a daily basis can be expected.

System imprecision increased with increasing frequency. This is expected, because the AC signal level decreases with increasing frequency. The errors below 50 MHz were comparable to the traditionally assumed measurement errors of 0.2 degrees and 0.005 in modulation. Since many lifetime based sensors show 30 degrees of phase shift and 0.40 change in modulation, these errors correspond to only a few percent error for sensing applications. The noise at 75 MHz can be unacceptable for critical experiments, but can still give only a 5% error for lifetime based sensors. Noise can be reduced further by increasing the sampling time. For the purpose of this exercise, readings were collected for about 12 seconds and averaged. Drift in the measurements can require frequent re-calibration against a known standard, similar to the setup used by conventional cross-correlation phase fluorometers.

Although the preferred embodiments of the present invention have been disclosed for illustrative purposes, those skilled in the art will appreciate that various modifications, additions and substitutions are possible without departing from the scope and spirit of the invention as disclosed in the accompanying claims.

What is claimed is:

1. A method for determining lifetimes of one or more photoluminescent species in a sample holder by measuring a phase angle and a modulation factor of the photoluminescent species comprising the steps of:
   providing an AC reference signal;
   providing a DC bias signal;
   disposing said photoluminescent species in the sample holder;
   biasing said AC reference signal with said DC bias signal to produce a biased AC input signal;
   modulating a light source at a frequency of said biased AC input signal to produce modulated exciting light having a wavelength capable of exciting said photoluminescent species;
   exciting said photoluminescent species in said sample holder with said modulated exciting light to produce a corresponding modulated light emission from said photoluminescent species;
   detecting said corresponding modulated light emission from said photoluminescent species;
   generating a modulated electrical emission signal indicative of said corresponding modulated light emission;
   processing said modulated electrical emission signal to obtain values of fluorescence lifetimes of said photoluminescent species.

2. The method of claim 1, wherein the processing comprises heterodyning and further comprises:
   splitting said modulated electrical emission signal into its AC and DC components, measuring said DC component, and mixing said AC component with an AC reference signal whereby a phase and amplitude information are shifted to a lower frequency signal; and
   sampling, filtering, applying offsets and analyzing said lower frequency signal to obtain a DC value wherein said DC value is indicative of values of fluorescence lifetimes of said photoluminescent species.

3. The method of claim 1, wherein the processing comprises homodyning and further comprises:
   splitting said modulated electrical emission signal into its AC and DC components, measuring said DC component, and mixing said AC component with AC reference signals and filtering and analyzing a resulting signal whereby a phase and amplitude information of said resulting signal are expressed as two DC values that are indicative of values of fluorescence lifetimes of said photoluminescent species.

4. The method of claim 1, wherein the processing comprises direct sampling and further comprises:
   splitting said modulated electrical emission signal into its AC and DC components, measuring said DC component, and filtering, sampling, and analyzing said AC component whereby a phase and amplitude information of said AC component are expressed as two DC values that are indicative of values of fluorescence lifetimes of said photoluminescent species.

5. A method of determining the lifetime of at least one photoluminescent species by measuring both a phase angle and modulation factor of the photoluminescent species comprising the steps of:

providing an AC reference signal;

providing a DC bias signal;

biasing said AC reference signal with said DC bias signal to produce a biased AC input signal;

modulating a light source at a frequency of said biased AC input signal to produce modulated exciting light having a wavelength capable of exciting said photoluminescent species;

disposing an analyte or sample of interest in a sample holder;

optically coupling a distal end of a first proximal arm of a bifurcated fiber optic to said modulated light source;

exposing a common end of said bifurcated fiber optic which has at least one photoluminescent species immobilized on its end, to said analyte or sample of interest disposed in said sample holder;

transmitting said modulated exciting light through said bifurcated fiber optic from the distal end of said first proximal arm optically coupled to said modulated light source to the common end of the bifurcated fiber optic;

exciting said photoluminescent species which is immobilized on said common end of the fiber optic and exposed to said analyte or sample of interest with said transmitted modulated exciting light, producing a corresponding emission from said photoluminescent species;

transmitting said modulated emission from said photoluminescent species disposed on said common end of the fiber optic to a distal end of a second proximal arm of the bifurcated fiber optic;

optically coupling the distal end of the second proximal arm of the bifurcated fiber optic to a detector;

detecting said emission from the distal end of the second proximal arm of the bifurcated fiber optic, producing a modulated electrical emission signal;

processing said modulated electrical emission signal to obtain values of fluorescence lifetimes of said photoluminescent species.

6. The method of claim 5, wherein said photoluminescent species is immobilized in a porous fiber, solid or gel matrix which is optically coupled to the common end of said bifurcated fiber optic and exposed to said analyte or sample of interest in said sample holder.

7. A phase fluorometer for determining lifetimes of at least one photoluminescent species by measuring both a phase angle and modulation factor of the photoluminescent species, said phase fluorometer comprising in combination:

means for generating an AC reference signal;

means for generating a DC bias signal;

means for generating an AC input signal;

a light source;

modulating means for modulating said light source, said modulating means including a mixing means for mixing a DC bias signal and a first AC reference signal to provide a modulated AC input signal to drive said light source;

a circuit connecting said modulating means and said light source;

detecting means for detecting photoluminescent light emitted by said photoluminescent species and producing a modulated electrical emission signal;

means for splitting said modulated electrical emission signal into an AC component and a DC component;

means for measuring said DC component;

means for processing said AC and DC components to obtain a DC value indicative of a value of the fluorescence lifetime of said photoluminescent species.

8. The phase fluorometer of claim 7, wherein said means for processing said AC and DC components further comprises:

means of mixing said AC component with a second AC reference signal whereby phase and amplitude information are shifted to a lower frequency signal;

means of sampling, filtering, applying offsets and analyzing said lower frequency signal to obtain a DC value wherein said DC value is indicative of a value of the fluorescence lifetime of said photoluminescent species;

a circuit connecting said means for splitting said modulated electrical emission signal into said AC component and said DC component with said means of mixing said AC component with said second AC reference signal whereby phase and amplitude information are shifted to a lower frequency signal;

a circuit connecting said means of mixing said AC component with said second AC reference signal whereby phase and amplitude information are shifted to a lower frequency signal with said means of sampling, filtering, applying offsets and analyzing said lower frequency signal to obtain a DC value wherein said DC value is indicative of a value of the fluorescence lifetime of said photoluminescent species.

9. The phase fluorometer of claim 8, wherein said means of mixing said AC component with said second AC reference signal whereby phase and amplitude information are shifted to a lower frequency signal, is a lock-in amplifier.

10. The phase fluorometer of claim 8, wherein said means of sampling, filtering, applying offsets and analyzing said lower frequency signal to obtain a DC value wherein said DC value is indicative of a value of the fluorescence lifetime of said photoluminescent species, is a lock-in amplifier.

11. The phase fluorometer of claim 7, wherein said means for processing said AC and DC components further comprises:

means of mixing said AC component with at least two AC reference signals to generate a resulting signal;

means of filtering and analyzing the resulting signal whereby phase and amplitude information of said resulting signal are expressed as two DC values that are indicative of values of the fluorescence lifetimes of said photoluminescent species;

a circuit connecting said means for splitting said modulated electrical emission signal into said AC component and said DC component with said means of mixing said AC component with said at least two AC reference signals to generate said resulting signal;

a circuit connecting said means of mixing said AC component with said at least two AC reference signals to generate said resulting signal with said means of filtering and analyzing the resulting signal whereby phase and amplitude information of said resulting signal are expressed as two DC values that are indicative of values of fluorescence lifetimes of said photoluminescent species.

12. The phase fluorometer of claim 11, wherein said means of mixing said AC component with said at least two AC reference signals to generate a resulting signal, is a lock-in amplifier.

13. The phase fluorometer of claim 11, wherein said means of filtering and analyzing the resulting signal whereby phase and amplitude information are expressed as two DC values that are indicative of values of the fluorescence lifetimes of said photoluminescent species, is a lock-in amplifier.

14. The fluorometer of claim 7, wherein said means for processing said AC and DC components further comprises:

means of filtering, sampling and analyzing said AC component whereby phase and amplitude information of said AC component are expressed as two DC values that are indicative of values of the fluorescence lifetimes of said photoluminescent species;

a circuit connecting said means for splitting said modulated electrical emission signal into said AC component and said DC component with said means of filtering, sampling and analyzing said AC component whereby phase and amplitude information of said AC component are expressed as two DC values that are indicative of values of the fluorescence lifetimes of said photoluminescent species.

15. The phase fluorometer of claim 14, wherein said means of filtering, sampling and analyzing said AC component whereby phase and amplitude information of said AC component are expressed as two DC values that are indicative of values of the fluorescence lifetimes of said photoluminescent species, is a lock-in amplifier.

16. The phase fluorometer of claim 7, wherein said means for generating an AC reference signal and for generating a DC bias signal is a lock-in amplifier.

17. The phase fluorometer of claim 7, wherein said modulating means is a bias tee.

18. The phase fluorometer of claim 7, wherein said detecting means is a photomultiplier tube.

19. The phase fluorometer of claim 7, wherein said means for splitting said modulated electrical emission signal into said AC component and said DC component is a bias tee.

20. The phase fluorometer of claim 7, further comprising:

a bifurcated fiber optic having a common end and two proximal arms;

means for optically coupling said common end of said bifurcated fiber optic to a sample holder;

means for optically coupling a distal end of a first proximal arm of said bifurcated fiber optic to said modulated light source;

means for optically coupling the distal end of the second proximal arm of said bifurcated fiber optic to said detecting means.

* * * * *